(12) United States Patent
Luber

(10) Patent No.: US 6,804,007 B2
(45) Date of Patent: Oct. 12, 2004

(54) APPARATUS FOR MULTIPLEXING TWO SURFACE PLASMA RESONANCE CHANNELS ONTO A SINGLE LINEAR SCANNED ARRAY

(75) Inventor: Edward Luber, Williamsville, NY (US)

(73) Assignee: Reichert, Inc., Depew, NY (US)

( * ) Notice: Subject to any disclaimer, the term of this patent is extended or adjusted under 35 U.S.C. 154(b) by 83 days.

(21) Appl. No.: 10/238,143

(22) Filed: Sep. 10, 2002

(65) Prior Publication Data

US 2004/0046962 A1 Mar. 11, 2004

(51) Int. Cl.[7] .............................................. G01N 21/55
(52) U.S. Cl. ...................................................... 356/445
(58) Field of Search ................................ 356/445, 446, 356/447, 448, 73

(56) References Cited

U.S. PATENT DOCUMENTS

| | | | |
|---|---|---|---|
| 4,889,427 A | 12/1989 | Van Veen et al. | 356/445 |
| 5,313,264 A | 5/1994 | Ivarsson et al. | 356/73 |
| 5,485,277 A | 1/1996 | Foster | 356/445 |
| 5,763,191 A | 6/1998 | Knoll et al. | 435/7.1 |
| 5,917,607 A * | 6/1999 | Naya | 356/445 |
| 6,441,906 B2 * | 8/2002 | Dickopf et al. | 356/445 |
| 6,569,383 B1 * | 5/2003 | Nelson et al. | 422/68.1 |
| 6,717,663 B2 * | 4/2004 | Atkinson et al. | 356/136 |
| 2003/0076501 A1 * | 4/2003 | Hofmann | 356/445 |

* cited by examiner

Primary Examiner—Michael P. Stafira
Assistant Examiner—Juan D Valentin, II
(74) Attorney, Agent, or Firm—Hodgson Russ LLP

(57) ABSTRACT

An apparatus for performing optical measurements comprising a light source operatively arranged to emit light along a beam path, a prism, a sensor chip mounted to a sample surface of the prism, and a detector operatively arranged to measure intensity of light reflected from the intermittent members of the metallic film. The sensor chip has a metallic film with a plurality of intermittent members, a first sample reservoir, and a second sample reservoir. The first and second reservoirs are operatively arranged to hold and position a sample on at least one member of a plurality of intermittent members of the metallic film.

15 Claims, 8 Drawing Sheets

APPARATUS FOR MULTIPLEXING TWO SURFACE PLASMA RESONANCE CHANNELS ONTO A SINGLE LINEAR SCANNED ARRAY

FIELD OF THE INVENTION

The present invention relates generally to optical instruments for measuring refractive index of a substance, and, more particularly, to an optical configuration and method for measuring a difference in refractive index between at least one test sample and a reference sample. The present invention is applicable to surface plasmon resonance (SPR) applications. Biosensors are measured with the use of SPR as well.

BACKGROUND OF THE INVENTION

The phenomenon of surface plasmon resonance, or SPR, is well known. SPR causes a drop in the intensity of light reflected from the interface of an optically transparent substance and a metal surface at a specific wavelength and angle of incidence. The location of the intensity minimum, measured with respect to wavelength of the incident light or the angle of incidence of the light with respect to the metal surface, changes when differing compositions of substances are placed in a sample space on the metal surface opposite the transparent substance. By measuring the location of the intensity minimum, the identity of the substance in contact with the metal surface may be determined.

Devices have been developed to use SPR in making optical measurements. More specifically, U.S. Pat. No. 5,313,264 to Ivarsson et al. describes an optical biosensor system that comprises a plurality of side-by-side sensing surfaces 39A–D illuminated by a streak of light 5 extending transversely across the sensing surfaces, and an anamorphic lens system 6 by which rays of light reflected from the respective sensing surfaces are imaged on corresponding columns of a two-dimensional array 7 of photosensitive elements. Accordingly, the signals from the photosensitive elements can be processed to determine a minimum reflectance associated with the resonance angle at each sensing surface. Although the system described in U.S. Pat. No. 5,313,264 avoids the use of moving parts, it is nevertheless optically complex and requires a two-dimensional array, factors that are accompanied by an increase in cost.

Finally, it is noted that one-dimensional (linear) arrays of photosensitive elements cells are commonly used in automatic refractometers designed to take non-differential readings with respect to a single test sample. Examples can be found in U.S. Pat. No. 4,640,616 (Michalik) and U.S. Pat. No. 6,172,746 (Byrne et al.). However, the patentee is unaware of any SPR measurement device that analyzes two samples simultaneously using a linear array, despite the recognized economy offered by this type of array.

Clearly, then, there is a longfelt need for an apparatus that can multiplex two SPR channels onto a single one-dimensional array.

SUMMARY OF THE INVENTION

The invention broadly comprises an apparatus for performing optical measurements having a light source operatively arranged to emit light along a beam path, a prism, a sensor chip mounted to a sample surface of the prism, and a detector operatively arranged to measure intensity of light reflected from the intermittent members of the metallic film. The sensor chip has a metallic film with a plurality of intermittent members, a first sample reservoir, and a second sample reservoir. The first and second reservoirs are operatively arranged to hold and position a sample on at least one member of a plurality of intermittent members of the metallic film.

The invention also broadly comprises a sensor chip for an optical instrument comprising a transparent member, a first and a second light reflective member, and a first and a second reservoir. The first light reflective member has a portion offset from the second light reflective member in a direction parallel to a meridional plane of the optical instrument. The second light reflective member has a portion offset from the first light reflective member in a direction parallel to the meridional plane of the optical instrument. The first reservoir is located above the first light reflective member and the second reservoir is located above the second light reflective member.

The invention also comprises a device for reflecting light in an optical instrument comprising at least two reservoirs located on a metallic film having a plurality of intermittent members operatively arranged to define at least two regions on a detector. Each of the at least two regions comprises light reflected from a member in communication with only one of the reservoirs.

Finally, the invention provides a method for performing optical measurements comprising the steps of directing a beam of light from a light source through a first face of a prism, reflecting a portion of the directed beam of light from a second face of the prism, and detecting the reflected light with a detector. The second face of the prism has a first and a second reservoir, each holding one of the two samples. The first reservoir is located above a first light reflective member and the second reservoir is located above a second light reflective member. The first light reflective member has a portion offset from the second light reflective member in a direction parallel to the meridional plane of the apparatus. The second light reflective member has a portion offset from the first light reflective member in a direction parallel to the meridional plane of the apparatus.

A general object of the present invention is to provide an apparatus for multiplexing two SPR channels onto a single linear scanned array.

These and other objects, features and advantages of the present invention will become readily apparent to those having ordinary skill in the art upon a reading of the following detailed description of the invention in view of the drawings and claims.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE PREFERRED EMBODIMENT

It should be appreciated that, in the detailed description of the invention that follows, like reference numbers on different drawing views are intended to identify identical structural elements of the invention in the respective views.

Figure 1:
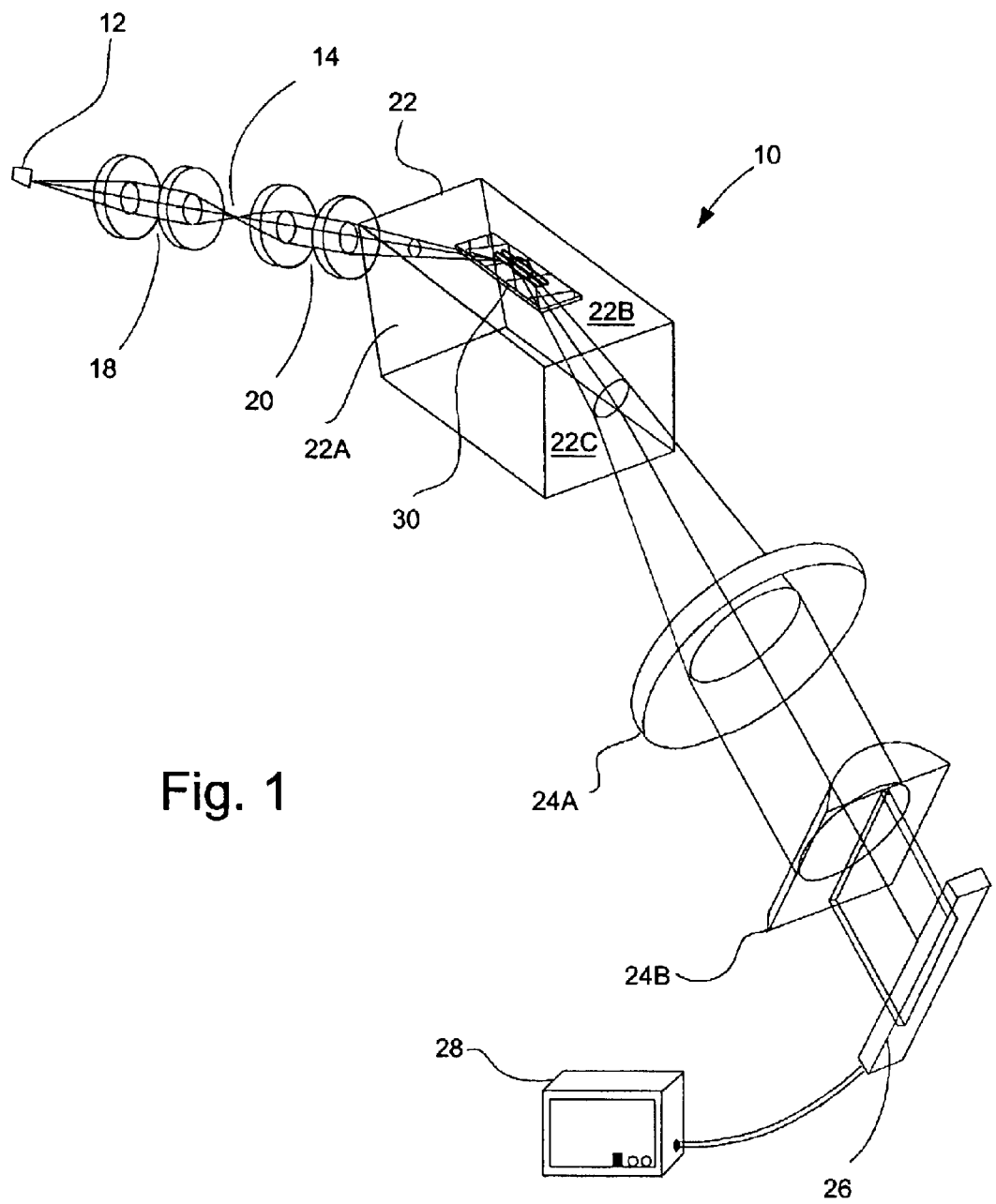
FIG. 1 is a perspective schematic view of a preferred embodiment of the present invention.
Figure 2A:
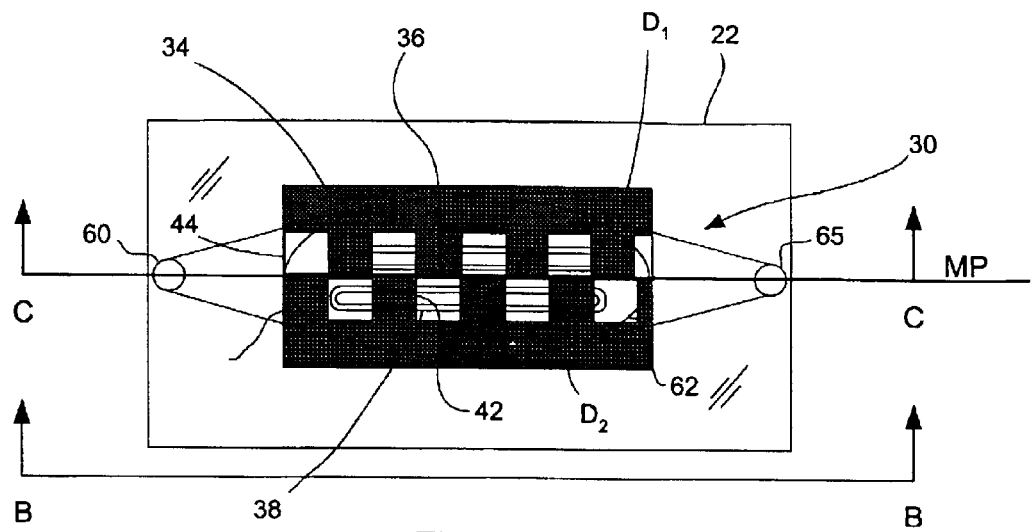
FIG. 2A is a top view of the prism and sensor chip of a preferred embodiment of the present invention, configured to hold two samples.

Adverting now to the drawings FIG. 1 illustrates SPR measurement apparatus 10 of the present invention. The SPR measurement apparatus 10 comprises a light source 12, focusing optics 18 and 20, a prism 22, a sensor chip 30 mounted to a sample surface 22B of the prism 22, first and second imaging optics 24A and 24B, detector 26, and processing electronics 28. Light is emitted by the light source 12 and travels along the beam path 14, defined by the light source 12 and focusing optics 18 and 20. Beam path 14 defines a meridional plane MP in which the beam path 14 resides, shown in FIG. 2A. The light emitted by light source 12 is focused by focusing optics 18 and 20 before it enters prism 22 through an entry face 22A. The circle 60 on FIG. 2A shows the width of the light beam as it traverses the entry face 22A. The light travels through a layer of transparent oil 50 between the sensor chip 30 and the sample surface 22B of the prism 22, shown in FIGS. 2B and 2C. The light continues through a transparent material 32 of the sensor chip 30 and is reflected by a metallic film 34 thereon. The region 62 on FIG. 2A shows the area wherein light is incident on the sample surface 22B. The reflection of the light by the metallic film 34 is affected by interaction of the incident light with the electron cloud of the metallic film 34. At certain wavelengths and angles of incidence, SPR results in the incident light being absorbed by the electrons in the metal, leading to a substantial drop in the intensity of the light reflected. The reflected light exits prism 22 through an exit face 22C and continues down beam path 14, through first and second imaging optics 24A and 24B to a detector 26. The circle 65 on FIG. 2A shows the beam width as the reflected light passes through the exit face 22C. In a preferred embodiment, the detector 26 is a one-dimensional scanned photodiode array, but it should be readily apparent to one having ordinary skill in the art that other detectors for determining the intensity of light are possible, and these modifications are within the scope of the invention as claimed. The wavelength of minimum reflectance may be found by varying the wavelength of the incident light while keeping the angle of incidence constant. Similarly, the angle of minimum reflectance may be found by varying the angle of incidence while keeping the wavelength constant. By comparing the location of the peak to the location of the peak for a substance of known refractive index, the refractive index of an unknown substance may be determined. Further, the presence of a substance in an unknown composition or the identity of an unknown composition may be determined by comparison of the SPR measurement results to the SPR measurement results for a known substance. These processes are well known in the art, and are detailed in U.S. Pat. No. 6,127,183, which is incorporated herein by reference.

In the present application, "angle of incidence" is intended to mean the angle between the plane containing the metallic film of the sensor chip and the light beam as it approaches the metallic film 34.

Figure 2B:
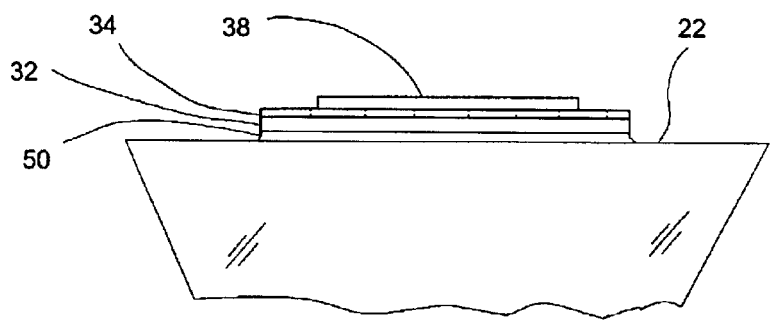
FIG. 2B is a side view of the prism and sensor chip of a preferred embodiment, taken at plane B—B of FIG. 2A.
Figure 2C:
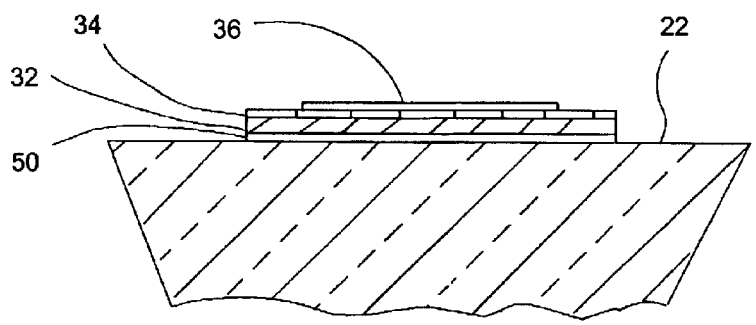
FIG. 2C is a cross sectional view of the prism and sensor chip of a preferred embodiment, taken at plane C—C of FIG. 2A.
Figure 3:
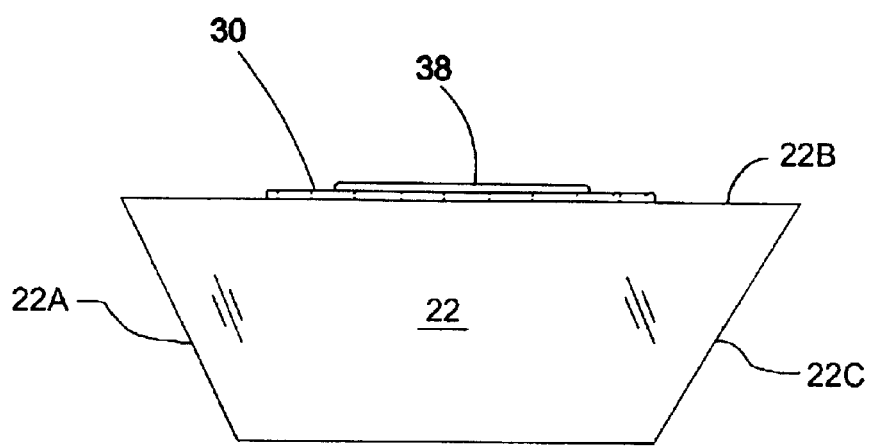
FIG. 3 is a side view of the sensor chip of an alternate embodiment of the present invention, configured to hold two samples.

Referring now to FIGS. 2A, 2B, and 2C, sensor chip 30 is provided with the thin metallic film 34 on one surface thereof. The surface of the sensor chip that bears the thin metallic film 34 is not in contact with sample surface 22B of prism 22 during SPR measurements. In a preferred embodiment, the metallic film 34 includes a layer of chromium approximately ten angstroms thick for adherence to the surface of glass slide 32, and a gold layer approximately fifty nanometers thick. A gasket material, such as room temperature vulcanizing (RTV) silicon, is applied to metallic film 34 to provide gaskets 36 and 38. The metallic film 34 is optically coupled, indirectly, to prism sample surface 22B through transparent glass slide 32 and a thin layer of transparent oil 50 provided between the underside of glass slide 32 and sample surface 22B. Of course, metallic film 34 can be optically coupled to the sample surface 22B by applying the film directly to the sample surface 22B, as illustrated in FIG. 3. This modification is intended to be within the scope of the invention as claimed.

In a preferred embodiment, the gasket 36 holds a test sample and the gasket 38 holds a reference sample, such that respective first and second optical interfaces are established. The gaskets are located such that the optical configuration is divided by the meridional plane MP into a test sample optical system on one side of the meridional plane and a reference sample optical system on the opposite side of the meridional plane. As light from illumination beam 12 reaches the metallic film 34 at the first optical interface, certain rays will be incident at a resonance angle determined by the refractive index of test sample and energy associated with such rays will be absorbed, while the remainder of the rays will be internally reflected by metallic film 34. In a similar manner at the second optical interface, certain rays will be incident at a resonance angle determined by the refractive index of reference sample and energy associated with such rays will be absorbed, while the remainder of the rays will be internally reflected by the metallic film 34.

As shown in FIGS. 2A, 2B, and 2C, the sensor chip 30 comprises transparent material 32 (e.g., glass), metallic film 34, and gaskets 36 and 38. Metallic film 34 comprises a plurality of metal members 42. Apertures 44 separate the metal members 42. The apertures 44 are gaps in the metallic film 34, exposing transparent material 32 beneath. Gaskets 36 and 38 are located over the metal members 42 and the apertures 44. Gaskets 36 and 38 each define a first and second reservoir, respectively, which receive and hold a sample to be analyzed by the SPR measurement apparatus 10 of the present invention. In the embodiment shown in FIG. 2A, the metal members 42 alternate with apertures 44 beneath gaskets 36 and 38. Light from the light source 12 is incident on the sensor chip 30 under both gaskets, but light is only reflected from metal members 42. Apertures 44 allow substantially all of the incident light to pass through the sensor chip and out of the system. The metal members 42 are arranged such that at least one metal member 42 under gasket 36 has a portion offset from the metal members 42 under gasket 38 in a direction parallel to the meridional plane MP of the SPR measurement apparatus. In a similar manner, at least one member under gasket 38 has a portion offset from the members under gasket 36 in a direction parallel to the meridional plane of the apparatus. Thus, there is at least one region on the detector 26 wherein the incident light is reflected from a metal member 42 beneath the first sample only, and there is at least one region on the detector 26 wherein the incident light is reflected from a metal member 42 beneath the second sample only.

Typically, transparent material 32 comprises glass. However, it should be readily apparent to one having ordinary skill in the art that other transparent material may be used, and these modifications are intended to be within the scope of the invention as claimed.

Metallic film 34 generally comprises silver or gold. However, it should be readily apparent to one having ordinary skill in the art that other metals may be used and these modifications are within the scope of the invention as claimed.

Figure 4:
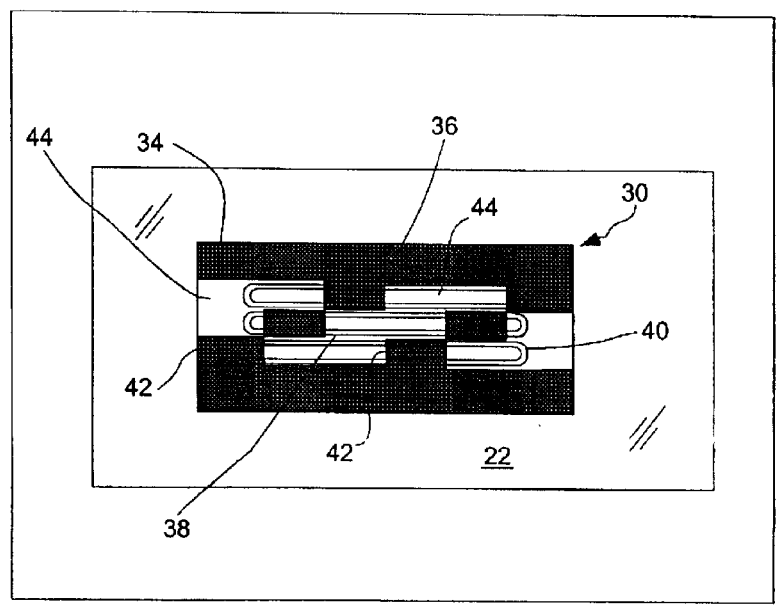
FIG. 4 is a top view of the sensor chip of a preferred embodiment of the present invention, configured to hold three samples.

The sensor chip 30 in FIG. 2A is configured to hold two samples. However, it should be readily apparent to one having ordinary skill in the art that configurations for holding three or more samples are possible, and these modifications are intended to be within the scope of the invention as claimed. FIG. 4 shows a sensor chip 30 arranged to hold three samples. Gaskets 36, 38, and 40 each define a first, second and third reservoir, respectively, for receiving and holding a sample to be analyzed by the SPR measurement apparatus 10. In this embodiment, metal members 42 are located beneath only one of the three samples along an axis parallel to the meridional plane MP. Apertures 44 are located beneath the other two gaskets. The light incident on the other two samples passes through an aperture 44 and out of the system. In this manner, the data from three samples is multiplexed onto detector 26 comprising a single one-dimensional array.

FIGS. 1–4 show gaskets 36, 38, and 40 that receive samples to be tested by the SPR measurement apparatus 10. However, it should be readily apparent to one skilled in the art that other reservoirs that can hold a sample on a surface are possible.

Figure 5:
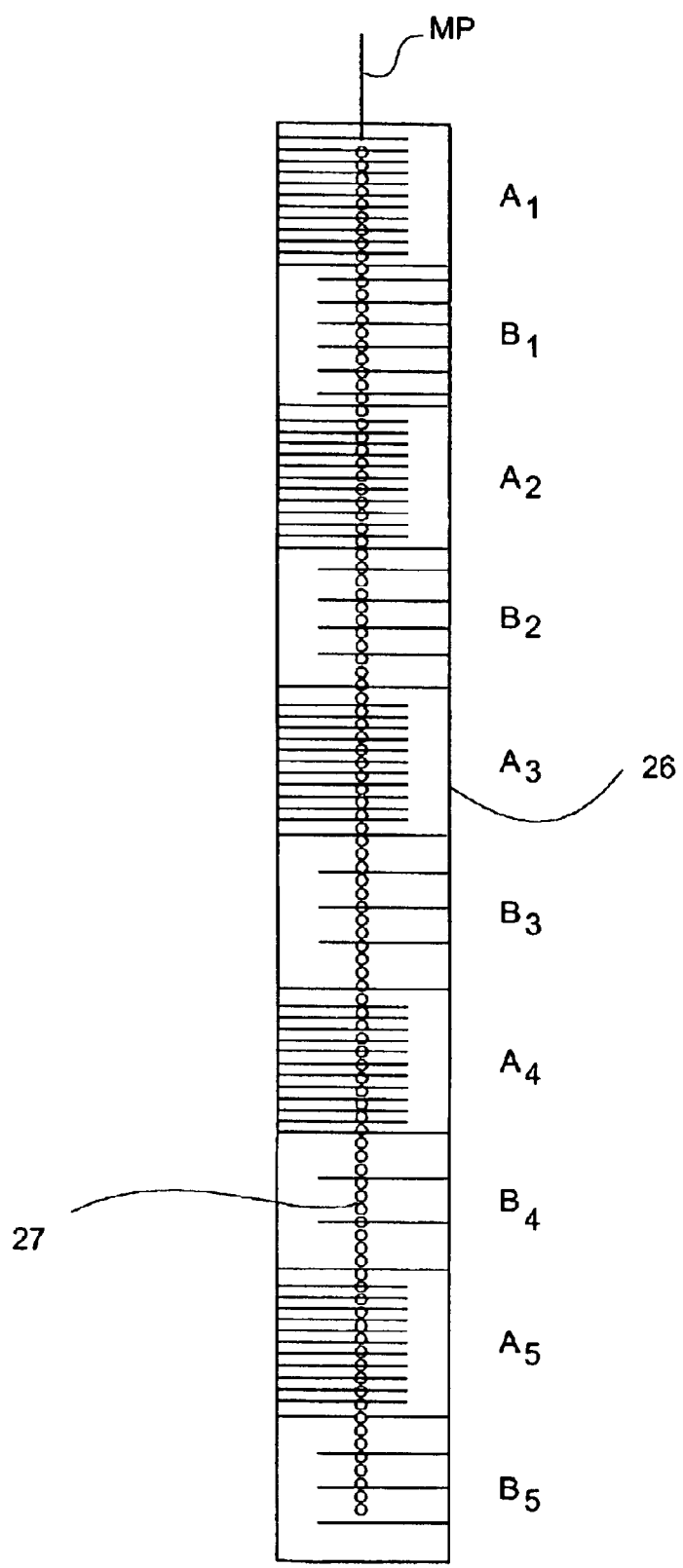
FIG. 5 is a front view of a detector of a preferred embodiment of the present invention.

As shown in FIG. 5, detector 26 comprises a plurality of linearly arranged photodiodes 27. The photodiodes 27 are preferably aligned to reside in meridional plane MP. Light reflected from the metal members 42 of the sensor chip 30 are focused by first and second imaging optics 24A and 24B and become incident on alternating regions A and B of the detector 26, shown in FIG. 5. Regions A of detector 26 receive light reflected from a first optical interface of a first sample in an SPR measurement apparatus 10 with two gaskets 36 and 38. (The first five regions A are designated $A_1$, $A_2$, $A_3$, $A_4$, and $A_5$.) Regions B receive light reflected from a second optical interface of a second sample in an SPR measurement apparatus 10 with two gaskets 36 and 38. (The first five regions B are designated $B_1$, $B_2$, $B_3$, $B_4$, and $B_5$.) In this manner, the data from the two samples is multiplexed onto the detector 26 comprising a single one-dimensional array. The size of detection regions A and B is proportional to the width of their corresponding metal members 42. The dimension referred to here as the "width" is shown on FIG. 2A as $D_1$ and $D_2$, respectively, for the width of the metal members 42 below gaskets 36 and 38, respectively. In a preferred embodiment, the width of the members are in a 1:1 proportion between any two of the at least two samples, leading to regions of equal size incident on the detector 26. For example, widths $D_1$ and $D_2$ are equal when the ratio of the widths of the members is 1:1. However, it should be readily apparent to one having ordinary skill in the art that other proportions could be used, and these modifications are intended to be within the scope of the invention as claimed. Also in a preferred embodiment, the width of the members is such that the members define detection regions extending 5–10 photodiodes 27 on the detector 26. In one embodiment, each photodiode 27 is 8 $\mu$m in the direction parallel to the axis of photodiodes 27, and 200 $\mu$m in the direction perpendicular to the axis of photodiodes 27.

In FIGS. 2A and 4, the metal members 42 are rectangular in shape. It should be readily apparent to one having ordinary skill in the art that other configurations and shapes are possible. Further, configurations having metal members 42 under both gaskets 36 and 38, leading to regions of the detector 26 receiving light from both samples, or configurations with apertures 44 under both gaskets 36 and 38, leading to regions of the detector 26 receiving light from neither sample, are possible. For these embodiments, processing electronics 28 would need to be programmed to ignore the data from those regions of the detector 26 not receiving light from any sample or receiving light from multiple samples.

Figure 6:
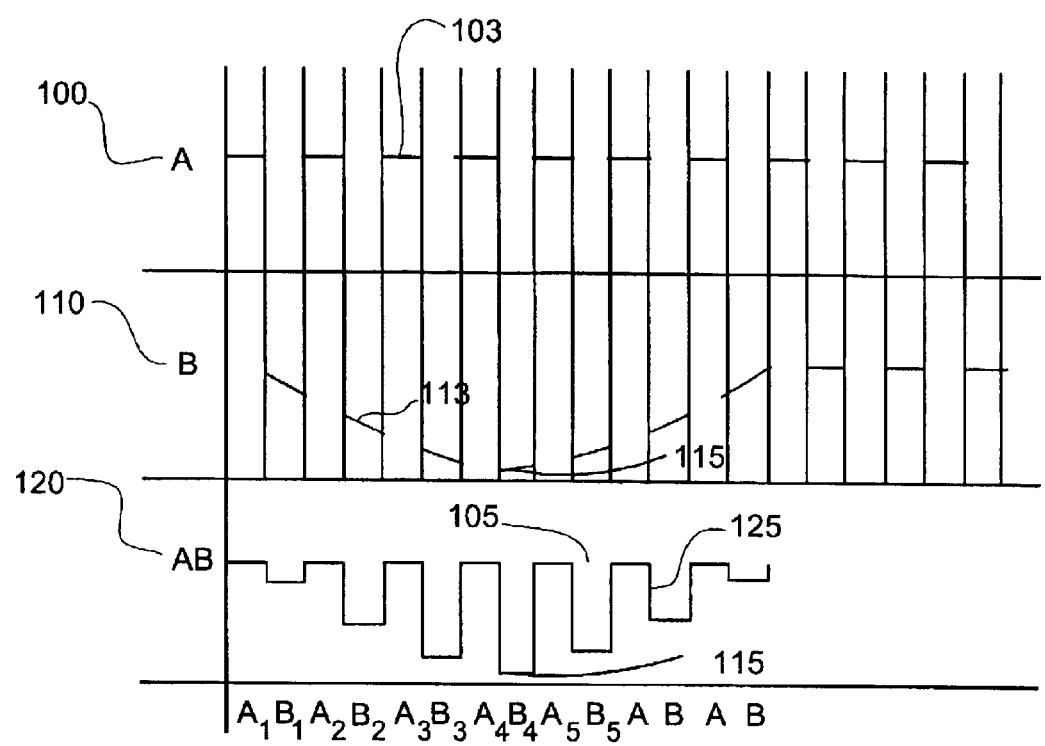
FIG. 6 is a graph showing the incident intensity spectra for two samples and a multiplexed spectrum measured by the detector.

Processing electronics 28, well known in the art, are programmed to separate the data from the multiple samples and determine the location of the minima in the light reflected from each sample. Typical individual spectra are shown multiplexed in FIGS. 6 and 7. Graph 100 of FIG. 6 shows intensity spectrum 103 for a first sample in the first gasket of an apparatus wherein the first gasket contains air, resulting in the same intensity of light being reflected across the entire spectrum. The first five detection regions of this spectrum for this sample, designated $A_1$, $A_2$, $A_3$, $A_4$, and $A_5$, respectively, are shown incident on detector 26 in FIG. 5.

Graph 110 of FIG. 6 shows intensity spectrum 113 for a second sample in a second gasket of an apparatus wherein the second gasket contains water. Since the light which hits the surface underneath the second gasket 38 encompasses a range of angles of incidence, the intensity profile for the area under the sample in second gasket 38 shows a minimum in the intensity of light reflected by the metal members 42 in the location where the film is hit by light fulfilling the SPR requirements, designated 115. The first five detection regions of this spectrum for this sample, designated $B_1$, $B_2$, $B_3$, $B_4$, and $B_5$, respectively, are shown incident on detector 26 in FIG. 5.

Graph 120 of FIG. 6 shows the multiplexed spectrum as measured by the SPR measurement apparatus 10. In a preferred embodiment, the electronics of the SPR measurement apparatus 10 average the intensity measured in each of the cells across each detection region, creating step function 125. The intensity minimum of each of the samples is determined from step function 125. Thus, the intensity minimum of each sample is measured by using a single one-dimensional detector.

Figure 7:
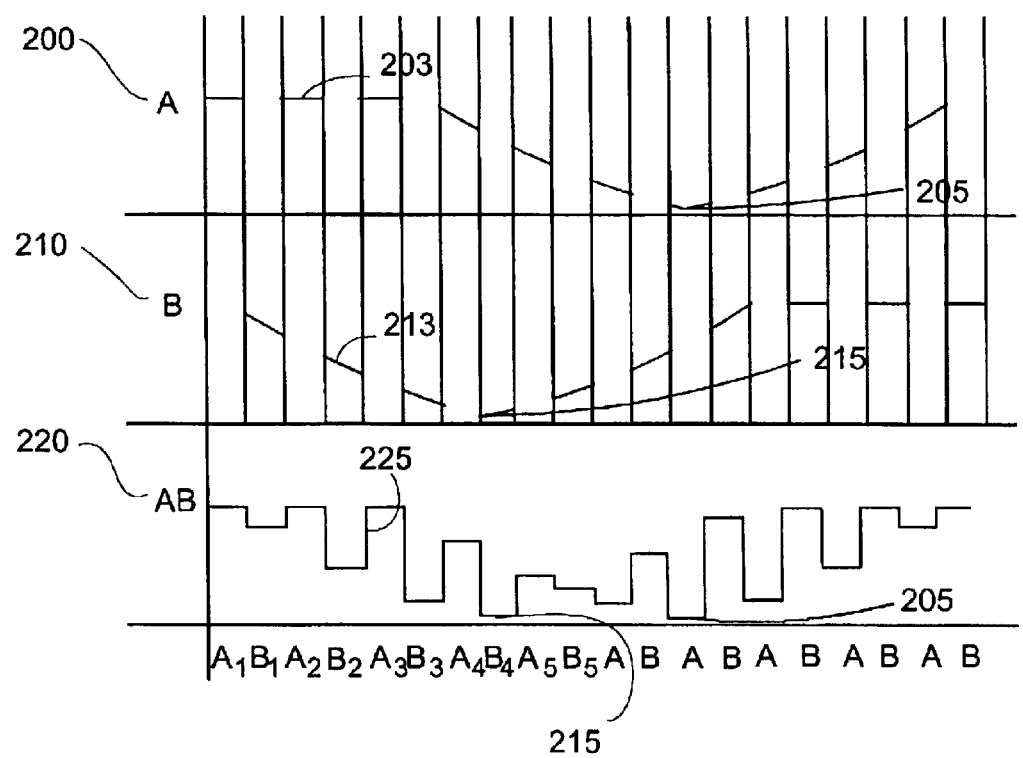
FIG. 7 is a graph showing the incident intensity spectra for two samples and a multiplexed spectrum measured by the detector; and, FIG. 8 is a front view of a detector of a preferred embodiment of the present invention.
Figure 8:
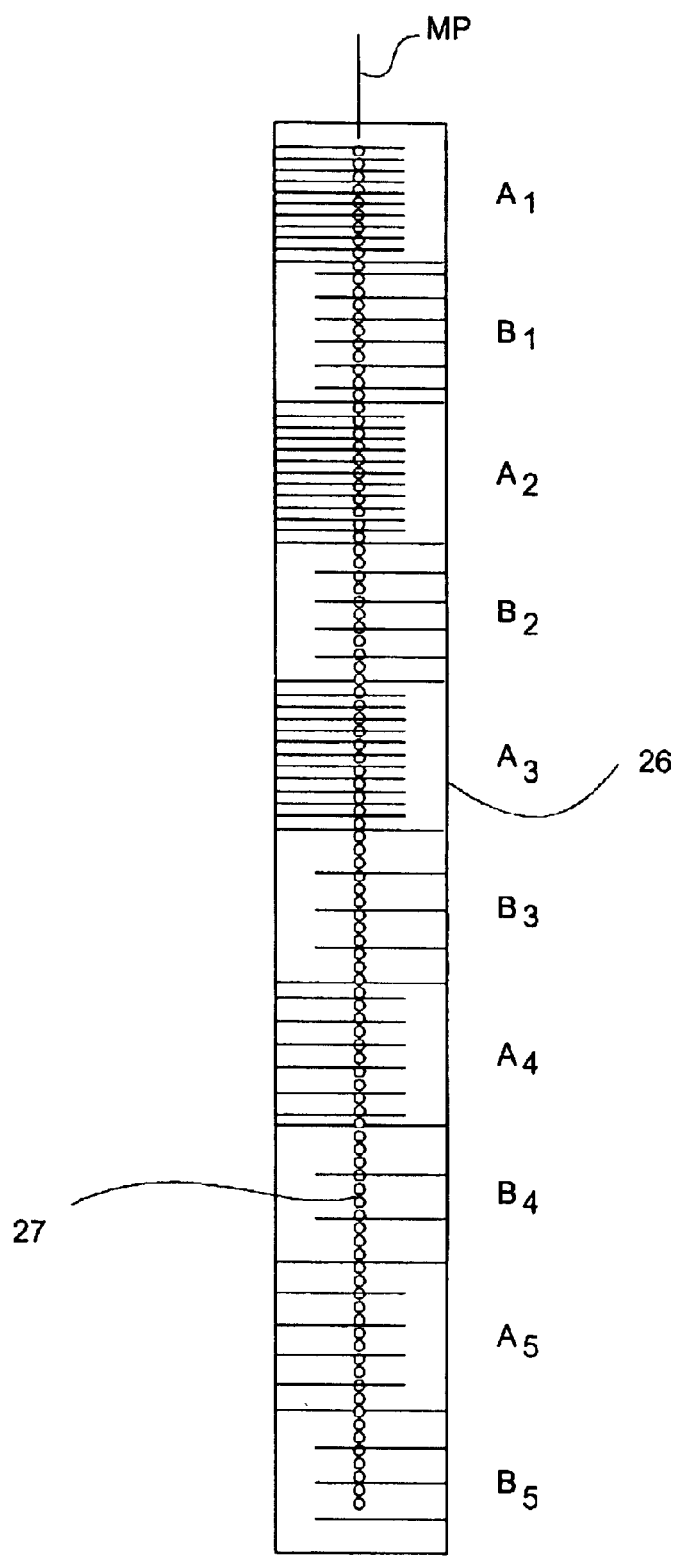

FIG. 7 shows the intensity of light reflected from the areas under the samples in first and second gaskets 36 and 38, respectively. Graph 200 of FIG. 7 shows the light intensity reflected from a first sample as a function of the location on the linear scanned array (LSA). First gasket 36 contains a buffer solution. Since the light which hits the surface underneath the first gasket 36 and the second gasket 38 encompasses a range of angles of incidence, incident intensity profiles 203 and 213 for the areas under the samples in first gasket 36 and second gasket 38 each show a minimum in the intensity of light reflected by the metal members 42 in the location where the film is hit by light fulfilling the SPR requirements. The intensity profile measured for the buffer solution in the first gasket is a step function that corresponds to the alternating pattern of metal members 42 and apertures 44 under first gasket 36. The step function is created by averaging the intensity values measured across each detection region. The intensity values are measured by the detector 26. As mentioned above, the light reflected from the areas under the samples in first gasket 36 and second gasket 38 is multiplexed onto the linear scanned array. On the linear scanned array, an alternating pattern of regions A and B is formed or imaged. The regions A correspond to the light reflected from the metal members 42 under first gasket 36 and the regions B correspond to the light reflected from the metal members 42 under second gasket 38. The first five detection regions for each sample, designated $A_1, A_2, A_3, A_4,$ and $A_5$, and $B_1, B_2, B_3, B_4,$ and $B_5$, respectively, on linear scanned array are shown on FIG. 8. Intensity profile 213 represents the intensity of light reflected from the metal members 42 under second gasket 38, which holds the sample to be measured and compared against the buffer sample. The second gasket 38 contains a sample of the buffer plus a protein. Minimum 215 in the intensity of light reflected by the metal members 42 under second gasket 38 is obtained for light which meets the angle of incidence for surface plasma resonance for the buffer plus protein solution. The intensity profile measured for the second sample is a step function that reflects the alternating pattern of metal members 42 under second gasket 38. Graph 220 of FIG. 7 shows in broken lines the intensity profiles 203 and 213 incident on regions A and B of linear scanned array 26. Also shown is step function 225 created by averaging the intensity values measured across each detection region. The minima 205 and 215 are determined from step function 225. Processing electronics 28 determine the minima of each of the spectra based on the geometry of the metal members 42 of the metallic film 34.

The present invention based on evanescent wave principles finds useful application in the observation of molecular interactions, particularly in the analysis of specific binding of analyte molecules to a binding layer. Accordingly, prepared slides having a predetermined, application-specific binding layer applied to metallic film 34 can be produced for use with a variety of analytes.

Thus, it is seen that the objects of the present invention are efficiently obtained, although modifications and changes to the invention should be readily apparent to those having ordinary skill in the art, and these modifications are intended to be within the scope of the invention as claimed.

What is claimed is:

1. An apparatus for performing optical measurements comprising:
    a meridional plane;
    a beam path in said meridional plane;
    a prism in said beam path, said prism including a sample surface extending in a plane orthogonal to said meridional plane;
    an intermittent metallic film associated with said sample surface, said intermittent metallic film forming a first pattern of reflective and transparent areas alternating along a direction parallel to said meridional plane and a second pattern of reflective and transparent areas alternating along said direction, wherein said reflective areas of said first pattern are alongside said transparent areas of said second pattern and said reflective areas of said second pattern are alongside said transparent areas of said first pattern, said first and second patterns being simultaneously illuminated by a beam of light on said beam path; and
    a light-sensitive detector arranged to receive light after reflection from said first pattern and from said second pattern.

2. The apparatus according to claim 1, wherein said intermittent metallic film is applied to a transparent slide placed on said sample surface.

3. The apparatus according to claim 1, wherein said intermittent metallic film is applied directly to said sample surface.

4. The apparatus according to claim 1, wherein said reflective and transparent areas of said first and second patterns are rectangular in shape.

5. The apparatus according to claim 4, wherein said reflective areas of said first pattern are of equal length in said direction parallel to said meridional plane and said transparent areas of said first pattern are of equal length in said direction parallel to said meridional plane.

6. The apparatus according to claim 4, wherein said reflective areas of said second pattern are of equal length in said direction parallel to said meridional plane and said transparent areas of said second pattern are of equal length in said direction parallel to said meridional plane.

7. The apparatus according to claim 4, wherein said reflective areas of said first and second patterns are of equal length in said direction parallel to said meridional plane and said transparent areas of said first and second patterns are of equal length in said direction parallel to said meridional plane.

8. The apparatus according to claim 1, wherein said first and second patterns are on opposite sides of said meridional plane.

9. The apparatus according to claim 8, wherein said light-sensitive detector comprises a linear array of photosensitive elements aligned in said meridional plane.

10. A sample slide for placement in a beam path of an optical instrument, said beam path residing in a meridional plane, said slide comprising:
    a transparent slide body including a slide surface having a longitudinal direction for alignment parallel to said meridional plane and a lateral direction for alignment normal to said meridional plane; and
    an intermittent metallic film applied to said slide surface, said intermittent metallic film forming a first pattern of reflective and transparent areas alternating along said longitudinal direction and a second pattern of reflective and transparent areas alternating along said longitudinal direction, wherein said reflective areas of said first pattern are alongside said transparent areas of said second pattern and said reflective areas of said second pattern are alongside said transparent areas of said first pattern.

11. The sample slide as defined in claim 10, further comprising a first fluid reservoir corresponding to said first pattern and a second fluid reservoir corresponding to said second pattern, whereby two different fluid samples can be brought into respective contact one with the first pattern and the other with the second pattern without said two fluid samples mixing.

12. The sample slide as defined in claim 10, wherein said reflective and transparent areas of said first and second patterns are rectangular in shape.

13. The apparatus according to claim 12, wherein said reflective areas of said first pattern are of equal length in said longitudinal direction and said transparent areas of said first pattern are of equal length in said longitudinal direction.

14. The apparatus according to claim 12, wherein said reflective areas of said second pattern are of equal length in said longitudinal direction and said transparent areas of said second pattern are of equal length in said longitudinal direction.

15. The apparatus according to claim 12, wherein said reflective areas of said first and second patterns are of equal length in said longitudinal direction and said transparent areas of said first and second patterns are of equal length in said longitudinal direction.

* * * * *